United States Patent
Chung et al.

(10) Patent No.: US 7,639,359 B2
(45) Date of Patent: Dec. 29, 2009

(54) MAGNETO-OPTIC BIOSENSOR USING BIO-FUNCTIONALIZED MAGNETIZED NANOPARTICLES

(75) Inventors: Seok-Hwan Chung, Rockville, MD (US); Axel F. Hoffmann, Chicago, IL (US); Samuel D. Bader, Oak Park, IL (US)

(73) Assignee: UChicagoArgonne, LLC, Chicago, IL (US)

( * ) Notice: Subject to any disclaimer, the term of this patent is extended or adjusted under 35 U.S.C. 154(b) by 174 days.

(21) Appl. No.: 11/875,475

(22) Filed: Oct. 19, 2007

(65) Prior Publication Data

US 2009/0033935 A1 Feb. 5, 2009

Related U.S. Application Data

(60) Provisional application No. 60/853,849, filed on Oct. 23, 2006.

(51) Int. Cl.
*G01N 21/00* (2006.01)
(52) U.S. Cl. ...................... 356/338; 356/337
(58) Field of Classification Search ......... 356/335–343; 250/458.1, 461.2; 324/204–205, 226, 232–234, 324/236, 239, 243, 248; 422/68.1; 436/526; 204/557; 385/12; 428/402
See application file for complete search history.

(56) References Cited

U.S. PATENT DOCUMENTS

| | | | |
|---|---|---|---|
| 5,922,537 A | * | 7/1999 | Ewart et al. .................. 435/6 |
| 6,825,655 B2 | | 11/2004 | Minchole et al. |
| 2004/0004043 A1 | * | 1/2004 | Terstappen et al. .......... 210/695 |
| 2007/0038121 A1 | * | 2/2007 | Feldman et al. ............. 600/476 |
| 2008/0296255 A1 | * | 12/2008 | Sailor et al. ................... 216/22 |

OTHER PUBLICATIONS

Magneto-optic measurement of Brownian relaxation of magnetic nanoparticles, S.H. Chung et al., J. Magnetism Magnetic Materials, 2007, doi:10.1016/j.jmmm.2007.05.016.

* cited by examiner

*Primary Examiner*—Gregory J Toatley, Jr.
*Assistant Examiner*—Tri T Ton
(74) *Attorney, Agent, or Firm*—Joan Pennington

(57) ABSTRACT

A biosensor utilizing bio-functionalized magnetic nanoparticles is provided. An external magnetic field is applied to a suspension of magnetic nanoparticles. A linearly polarized incident light is applied to the suspension of magnetic nanoparticles. A photocurrent from polarized light scattering by bio-functionalized magnetic nanoparticles in liquid is detected. The magneto-optic sensing technique is applied to a micro-fluidic channel for rapid and sensitive detection with a small sample amount, and subsequent magnetic separation for detoxification. This technique is used for the detection of Brownian relaxation with time sweep as well as frequency sweep. The magneto-optical sensor enables rapidly detecting changes in local dynamic properties of the magnetic nanoparticles in liquids and magnetic modulation of ferromagnetic particles in liquid provides increased signal sensitivity.

18 Claims, 6 Drawing Sheets

MAGNETO-OPTIC BIOSENSOR USING BIO-FUNCTIONALIZED MAGNETIZED NANOPARTICLES

This application claims the benefit of U.S. Provisional Application No. 60/853,849, filed on Oct. 23, 2006.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

FIELD OF THE INVENTION

The present invention relates to an improved biosensor that is sensitive, fast and cost effective, and more particularly to an improved biosensor that utilizes bio-functionalized magnetic nanoparticles.

DESCRIPTION OF THE RELATED ART

A need exists to develop improved biological sensors, which are sensitive, fast, cost-effective and capable of utilization by relatively untrained personnel, for example, in an effort to combat bio-terrorism and develop point-of-service biomedical applications.

Magnetic nanoparticles are receiving increased attention recently due to both fundamental scientific interest and their potential applications in magnetic data storage, actuators, and biosensors. The long-range interaction between magnetic nanoparticles and an external magnetic field enables manipulation and sensitive detection of those particles for such applications. Also the recent development of bio-conjugated magnetic nanoparticles provides various opportunities for the application of magnetic nanoparticles in the biomedical field. The shelf-life of magnetic nanoparticles can be essentially infinite, which is beneficial compared to other materials for biosensing such as fluorescent and radioactive materials.

In particular, the use of magnetic labels for sensing applications has generated widespread research efforts. In most conventional substrate-based sensing schemes, the absence or presence of magnetically labeled targets is verified via the detection of the magnetic stray field by means of the giant magnetoresistance, anisotropic magnetoresistance, Hall effect or superconducting quantum interference devices.

Among recent developments is a substrate-free biosensing approach based on Brownian relaxation of magnetic nanoparticles with biological surfactant suspended in liquid. This approach relies on detecting the modification of the Brownian motion of magnetic nanoparticles when they bind to selective targets in liquid solution.

U.S. Pat. No. 6,825,655 to Minchole et al., issues Nov. 30, 2004 is entitled "Method and arrangement for detecting changes of a magnetic response in magnetic particles." A method is disclosed for detecting changes of magnetic response of at least one magnetic particle provided with an external layer in a carrier fluid. The method comprising measuring the characteristic rotation time of the magnetic particle with respect to the external layer, and measuring Brownian relaxation in the carrier fluid under the influence of an external alternating magnetic field. The method implies that upon modification of the effective volume of the particle or its interaction with the carrier fluid, a hydrodynamic volume of the particle changes, which implies a change of the frequency ($f_{max}$) at which an out of phase component of the magnetic susceptibility has its maximum.

For example, a magnetite nanoparticles between 10 and 40 nanometers across coated with avidin, a glycoprotein that has a very strong affinity for biotin, for example, which is 30 nm thick has a specific peak in the magnetic susceptibility verses frequency curve. When biotin, a protein, which interacts with avidin was added, the change in the hydrodynamic radius, about 10 nm, changed the susceptibility verses frequency curve making the addition of the protein detectable.

This approach has advantages due to the stability of magnetic nanoparticles and the simplicity of the process. In this sensor, the binding of a biological target to the nanoparticles modifies the measurable dynamic magnetic properties, since the binding reaction increases the hydrodynamic radius, which results in an increased relaxation time. The signal is based on a change of the ac magnetic susceptibility upon binding to the target biological molecules, which can be measured with a pair of excitation and pick-up coils. A problem with this technique is that it is not sensitive as compared with other presently available sensors and detection takes on the order of 30 minutes.

A need exists for an improved biosensor that is sensitive, fast and cost effective.

A principal aspect of the present invention is to provide an improved biosensor that utilizes bio-functionalized magnetic nanoparticles.

Other important aspects of the present invention are to provide such an improved biosensor that utilizes bio-functionalized magnetic nanoparticles substantially without negative effect and that overcome some of the disadvantages of prior art arrangements.

SUMMARY OF THE INVENTION

In brief, a biosensor that utilizes bio-functionalized magnetic nanoparticles is provided. An external magnetic field is applied to a suspension of magnetic nanoparticles. A linearly polarized incident light is applied to the suspension of magnetic nanoparticles. A photocurrent from polarized light scattering by bio-functionalized magnetic nanoparticles in liquid is detected.

In accordance with features of the invention, the applied magnetic field causes field induced optical anisotropy originating from internal optical anisotropies, and surface or shape anisotropies of individual nanoparticles. Such anisotropy in magnetic nanoparticles causes dichroism and birefriengence of linearly polarized incident light, which are used to sense the changes of Brownian relaxation upon biological bindings in liquid environments.

In accordance with features of the invention, the magneto-optic sensing technique is applied to a micro-fluidic channel for rapid and sensitive detection with a small sample amount, and subsequent magnetic separation for detoxification. This technique is used for the detection of Brownian relaxation with time sweep as well as frequency sweep.

In accordance with features of the invention, the biosensor is a magneto-optical sensor that enables rapidly detecting changes in local dynamic properties of the magnetic nanoparticles in liquids. Further magnetic modulation of ferromagnetic particles in liquid potentially increases the signal sensitivity by several orders of magnitude as compared to the known or conventional ac magnetic susceptibility measurements. A possibility exists for in-vitro applications, such as detection of local temperature and viscoelasticity within inter-cellular environments.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In accordance with features of the invention, a magneto-optic sensing technique is based upon the detection of a photocurrent from polarized light scattering by bio-functionalized magnetic nanoparticles in liquid.

In accordance with features of the invention, the applied magnetic field causes field induced optical anisotropy originating from internal optical anisotropies, and surface or shape anisotropies of individual nanoparticles. Such anisotropy in magnetic nanoparticles causes dichroism and birefriengence of linearly polarized incident light, which are used to sense the changes of Brownian relaxation upon biological bindings in liquid environments.

In accordance with features of the invention, the magneto-optic sensing technique is applied to a micro-fluidic channel for rapid and sensitive detection with a small sample amount, and subsequent magnetic separation for detoxification. This technique advantageously is used for the detection of Brownian relaxation with time sweep as well as frequency sweep.

Figure 1:
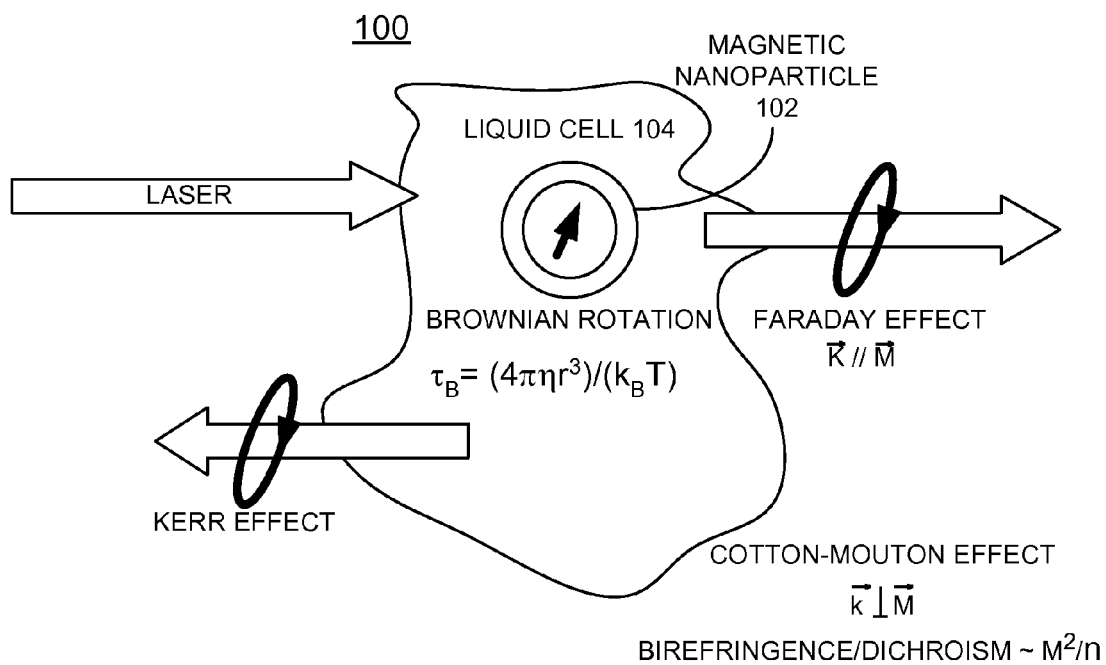
FIG. 1 is a schematic diagram representation illustrating magneto-optic biosensor in accordance with the preferred embodiment.

Having reference now to the drawings, in FIG. 1 there is schematically shown magneto-optic biosensor arrangement generally designated by the reference character 100 in accordance with the preferred embodiment. A plurality of magnetic nanoparticles 102 is suspended in a liquid or cell generally designated by the reference character 104. An external magnetic field is applied to the suspension of magnetic nanoparticles 102 in the liquid or cell 104. A linearly polarized incident light is applied to a colloidal suspension of magnetic nanoparticles, as indicated by a beam labeled Laser. Photocurrent from polarized light scattering by bio-functionalized magnetic nanoparticles in liquid is detected in accordance with the preferred embodiment of the invention.

Nanoparticles suspended in a liquid exhibit both random rotational diffusion and translational motion due to thermal fluctuations. For the rotational diffusion (Brownian rotation), the relaxation time is given by:

$$\tau_B = \frac{3\eta V}{k_B T} \quad (1)$$

where $\eta$ is the dynamic viscosity of the liquid, V is the hydrodynamic volume of the nanoparticle, and T is temperature. For magnetic nanoparticles with large enough anisotropy, the magnetization is blocked inside the nanoparticle. Therefore, in this case, the Brownian relaxation in the frequency domain can be measured directly by the imaginary part of the ac magnetic susceptibility as a function of frequency $\omega$ expressed as:

$$\chi''(\overline{\omega}) = \frac{\chi_0(\overline{\omega}\tau)}{1+(\overline{\omega}\tau)^2} \quad (2)$$

where $\chi_0$ is the static susceptibility and $\tau$ is the effective relaxation time of the nanoparticles. Note that $\chi''$ has a maximum when $\overline{\omega}=1/\tau$. For particles with polydispersity, Equation 2 should become an integral over the particle size dispersion function.

The conventional method for measuring the ac susceptibility is based on magneto-electric techniques. The principle is to measure the sample's magnetic response—amplitude and phase—with two detection coils while applying a small ac magnetic field to the sample by an ac drive and compensation coils. Recently this technique has been adopted for biological sensing using bio-functionalized magnetic nanoparticles in liquid. The change of ac susceptibility upon binding to biological target molecules is observed as a decrease of the frequency for the peak of $\chi''$ which depends on the effective Brownian relaxation time determined by the hydrodynamic size of the nanoparticles. There have been several alternative approaches proposed to measure ac susceptibility using magneto-optical effects (Faraday or Cotton-Mouton effect). These techniques have also been used to detect the binding of biological molecules to magnetic nanoparticles by time-dependent birefringence, which is related to the Brownian relaxation. However, there has not been any systematic effort to compare magneto-electric and magneto-optic approaches and discuss their possible applications.

It has been experimentally demonstrated in accordance with the present invention, the correspondence in ac susceptibility data obtained by both techniques using the same set of samples, and compare the sensitivity of the two techniques with an emphasis on the advantages of the optical method for advanced applications. The magneto-optical method of the invention combines the sensitivity of the optical technique and the suitability of a magnetism-based sensing scheme for the highly localized detection of the dynamic magnetic response.

A colloidal suspension of magnetic nanoparticles is known to become optically anisotropic upon application of an external magnetic field. This optical anisotropy can originate from field-induced effects, internal optical anisotropies, and surface anisotropies or shape anisotropies of the individual nanoparticles. The optical anisotropy induced in a suspension of magnetic nanoparticles causes a change in both the eigenmodes of radiation in the medium and in the polarization of linearly polarized incident light upon transmission. When a weak external magnetic field is applied parallel to the wave vector, the polarization of the incident beam rotates by:

$$\phi_F=VtH \quad (3)$$

where t is the sample thickness, H is the applied magnetic field, and V is the Verdet constant, which depends on the magnetization and the magnetic anisotropy, and the wavelength of the incident beam. When an alternating magnetic field is applied to the sample, the Faraday rotation angle, proportional to the dynamic magnetic susceptibility of the sample, changes correspondingly.

Figure 2:
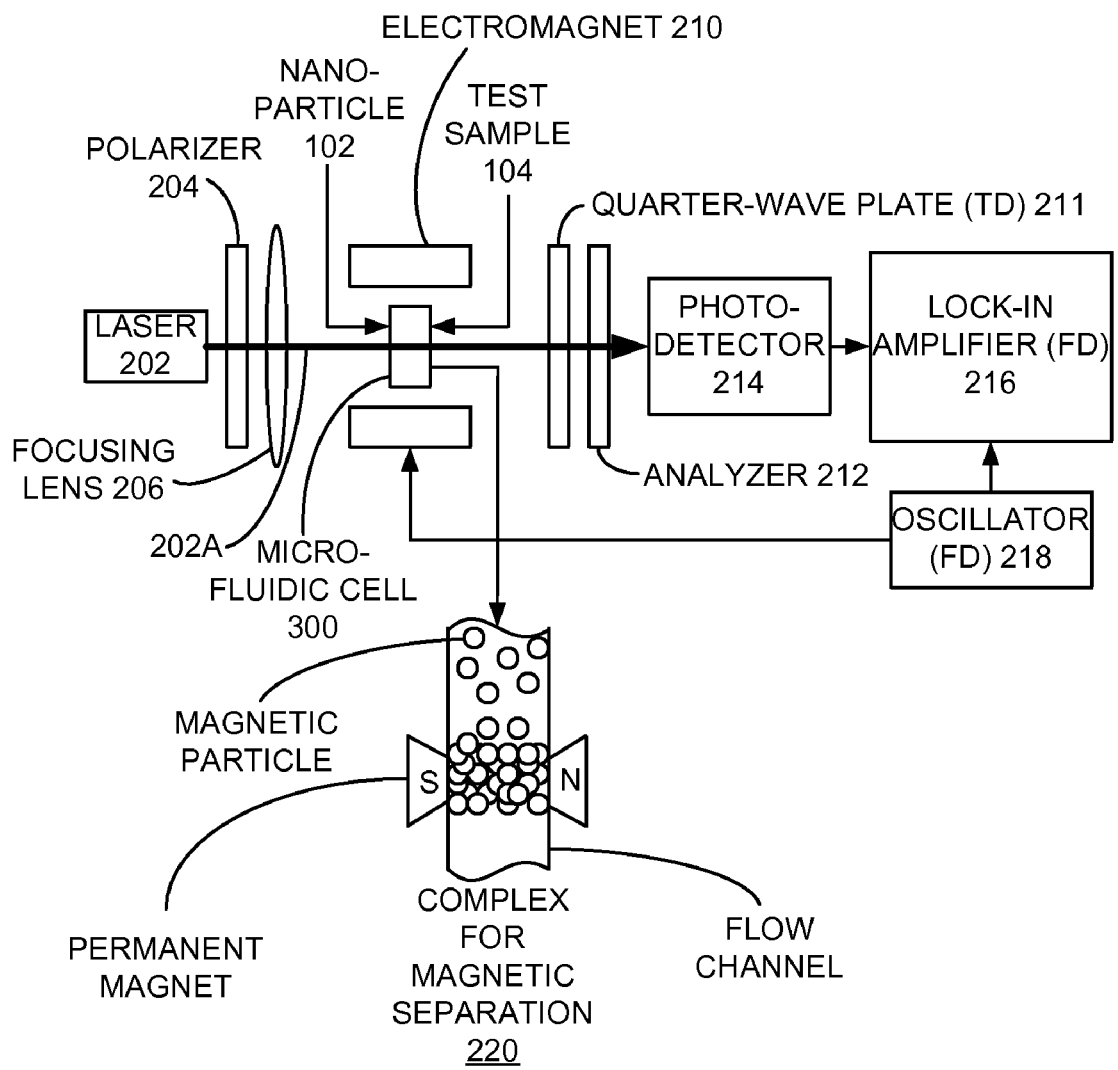
FIG. 2 is a schematic and block diagram representation illustrating exemplary apparatus for implementing a magneto-optic biosensor in accordance with the preferred embodiment.

Referring now to FIG. 2, there is shown exemplary apparatus for implementing a magneto-optic biosensor generally designated by the reference character 200 in accordance with the preferred embodiment. Exemplary experimental apparatus is shown in FIG. 2.

Figure 3:
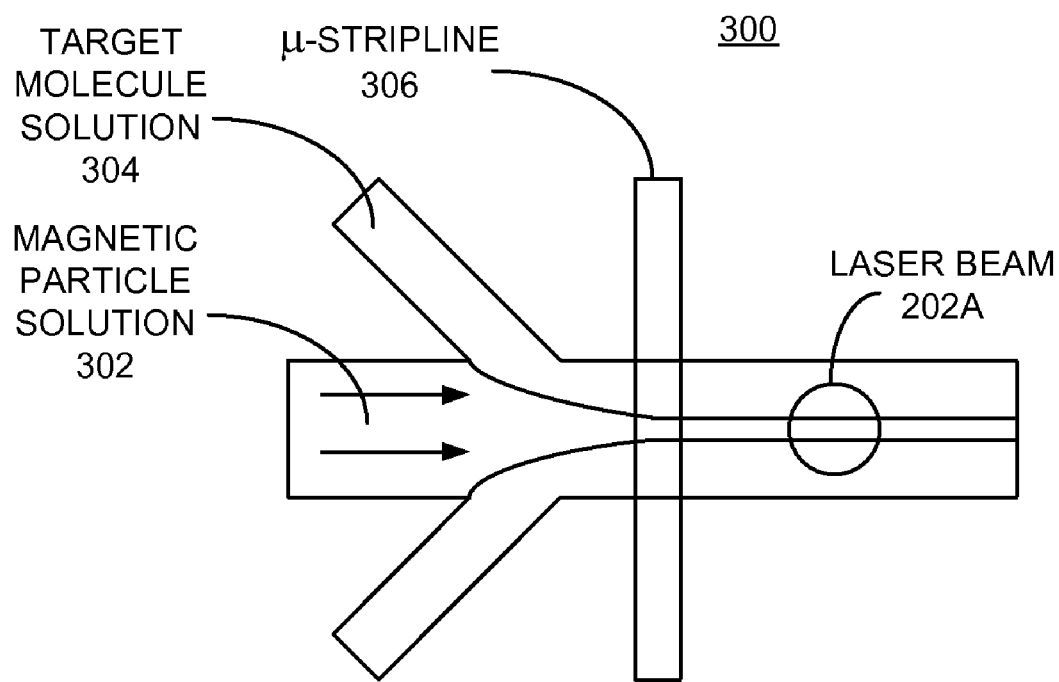
FIG. 3 is a schematic diagram representation illustrating an exemplary micro-fluidic cell of the apparatus for implementing a magneto-optic biosensor of FIG. 2 in accordance with the preferred embodiment.

The nanoparticle suspension 102 is contained within an optical liquid cell, such as a micro-fluidic cell 300 as illustrated and described with respect to FIG. 3. A light source or laser 202 provides a laser beam 202A in an optical path defined by a polarizer 204 and a focusing lens 206. The nanoparticle suspension 102 within an optical liquid cell or micro-fluidic cell 300 is placed in an electromagnet 210 or solenoid. An axial magnetic field of 10 Oe produced by the electromagnet 210 or solenoid is modulated by a frequency oscillator 218 in the range between 10 Hz and 5 kHz.

For example, the light source 202 is a Krypton laser with 530.9 nm wavelength and ~100 mW power. The fluctuation of the laser intensity is attenuated by an intensity stabilizer (CRI, Ltd.) whose feedback controls the intensity via an electro-optic modulator and temperature-controlled monitor photodiode. The laser beam is focused down to ~200 μm in diameter with the focusing lens 206. The polarization angle of the incident light is adjusted using a quarter-wave plate 211 so that the Faraday angle is within the weak field (linear) regime and applied to an analyzer 212. The modulated intensity due to the magneto-optic response is amplified by a photo detector 214. A lock-in amplifier 216 is used to measure the in-phase and out-of-phase components of the modulated intensity, proportional to the Faraday rotation, with respect to the reference signal measured by a high-frequency Gauss meter. The configuration of the setup can be modified to detect Brownian relaxation in time sweep upon removing external magnetic field. The Brownian relaxation can alternatively be detected by the magneto-optical birefringence measurement with external magnetic field applied perpendicular to the laser beam and a quarter-wave plate added as shown in FIG. 2. The magneto-optic biosensor 200 includes a complex for magnetic separation which is generally designated by the reference character 220.

Referring to FIG. 3, there is shown an exemplary microfluidic cell generally designated by the reference character 300 of the magneto-optic biosensor 200 of FIG. 2. The micro-fluidic cell 300 includes a micro-fluidic capillary network including a capillary receiving a solution of magnetic nanoparticles 302, and a capillary receiving a target molecule solution 304. The micro-fluidic capillary network 300 includes a μ-stripline 306. The laser beam 202A is shown applied to the combined magnetic nanoparticles 302 and target molecule solution 304.

Figure 4:
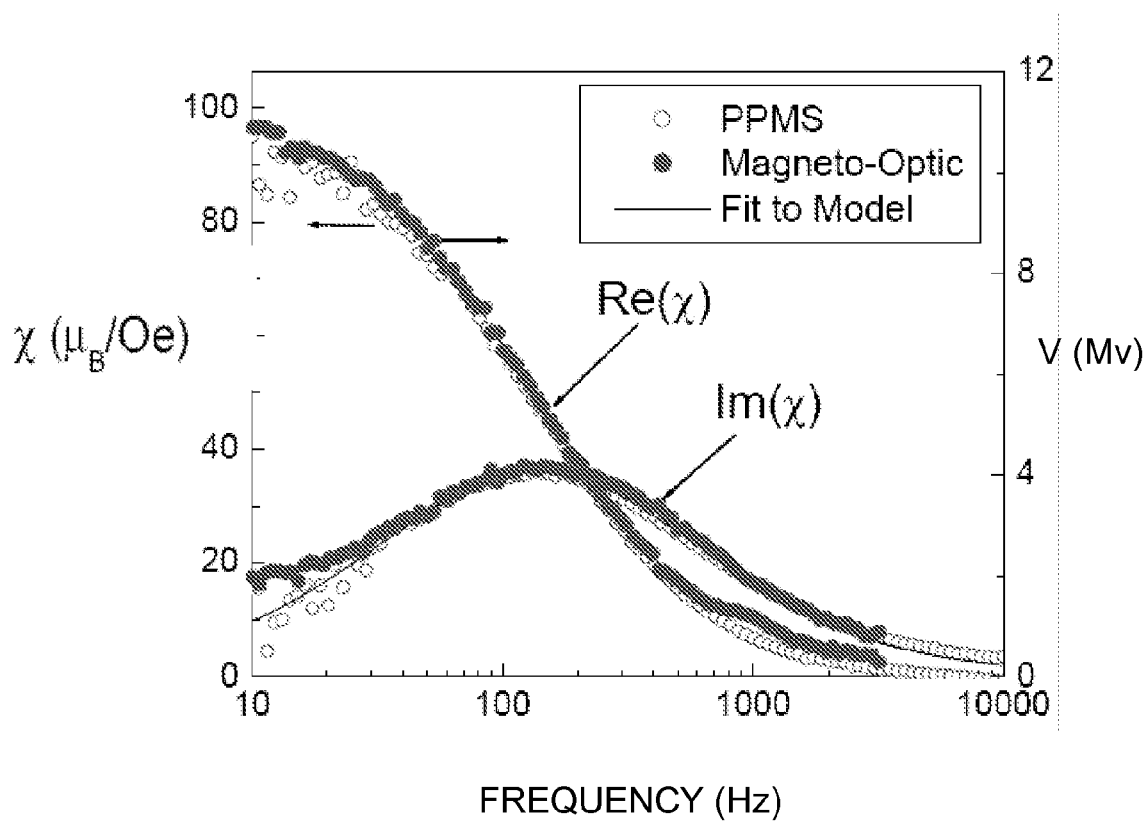
FIGS. 4, 5, and 6 are charts respectively illustrating exemplary operation of the apparatus for implementing a magneto-optic biosensor of FIG. 2 in accordance with the preferred embodiment.
Figure 5:
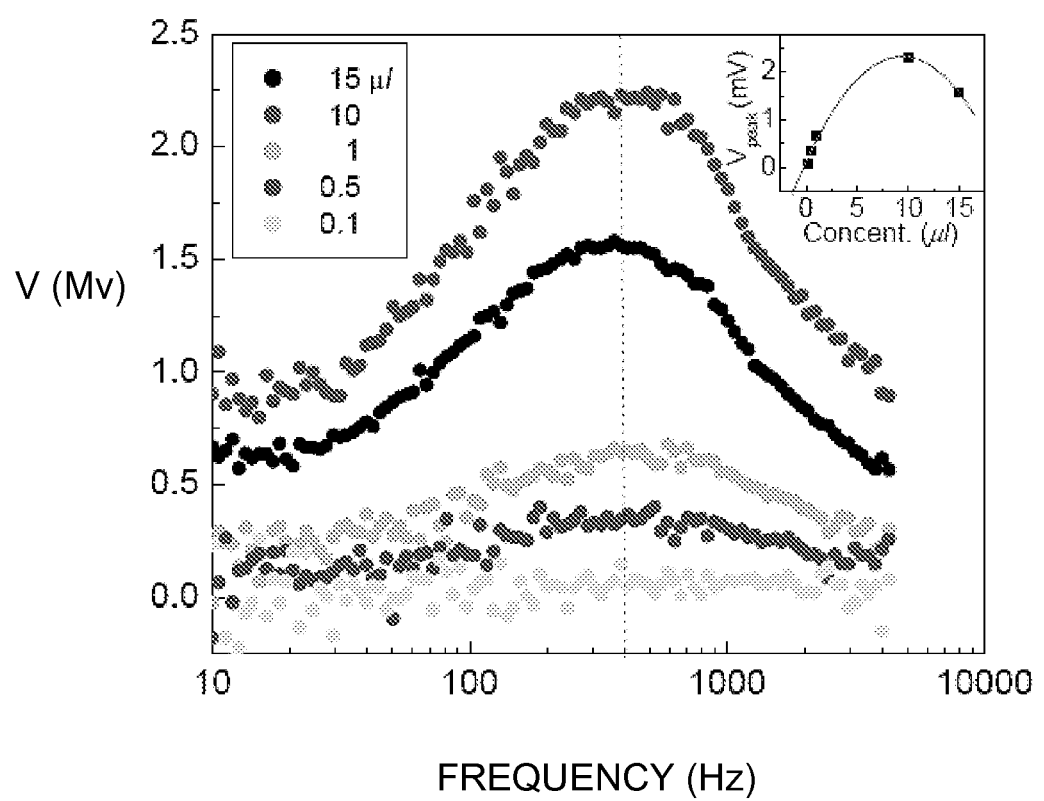
Figure 6:
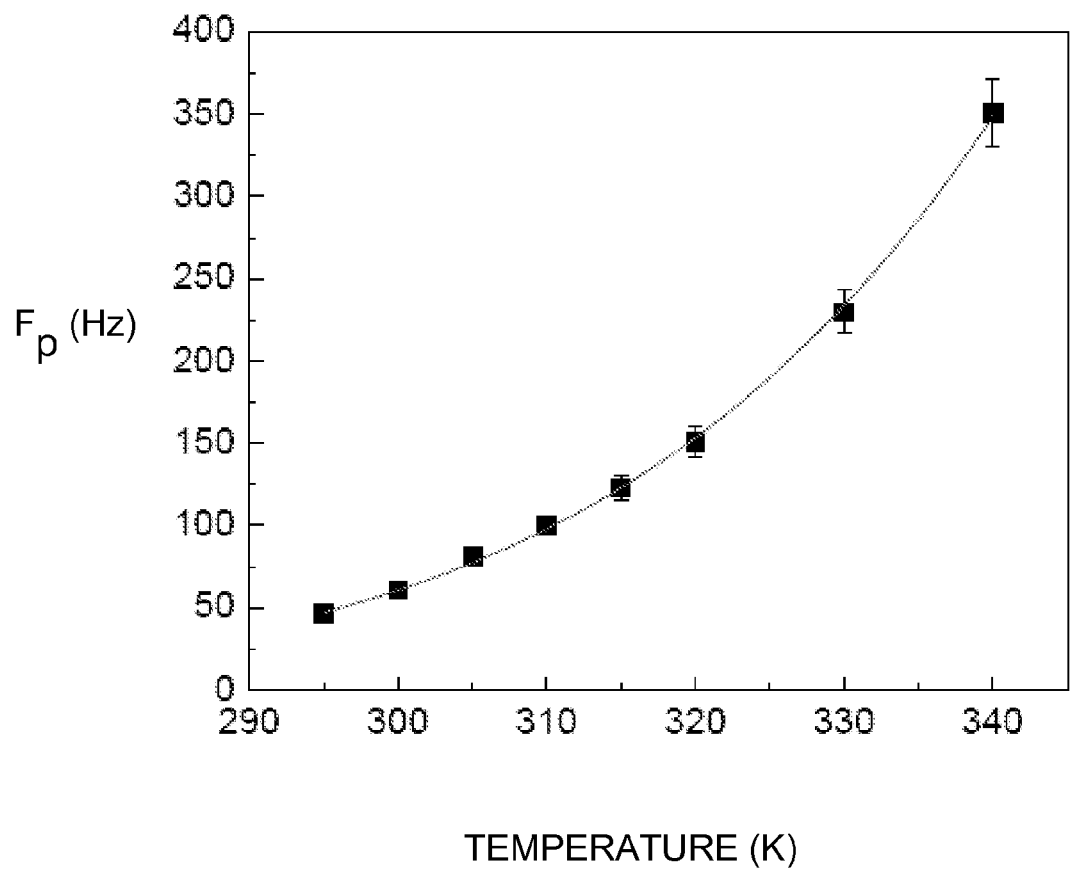

Referring also to FIGS. 4, 5, and 6 are charts respectively illustrating exemplary operation of the magneto-optic biosensor 200 of FIG. 2 in accordance with the preferred embodiment.

All the measurements were taken at room temperature (~23° C.). The magnetic nanoparticles used for the demonstration are $CoFe_2O_4$ particles with median diameter of 13 nm. The surface of the particles is chemically treated so that the nanoparticles are water-soluble. A room temperature hysteresis curve measured with a commercial physical property measurement system (PPMS) shows paramagnetic behavior, which is due to the Brownian relaxation of single domain nanoparticles in the liquid. The magnetic moment of each particle, estimated from a fitting to the Langevin function of paramagnetism, is $5.6 \times 10^4 \mu_B$. This value corresponds well to $5.3 \times 10^4 \mu_B$ estimated for a spherical single domain nanoparticle with a 13-nm diameter. Further, $CoFe_2O_4$ nanoparticles 13 nm in diameter are expected to be ferromagnetically stable due to their high anisotropy, and at the same time they should be single domain.

FIG. 4 shows the real and imaginary part of the ac susceptibility as a function of frequency measured magneto-electrically using the PPMS and also magneto-optically.

For the ac susceptibility measurement with the PPMS, a modulation field of 10 Oe was applied in the frequency range between 10 Hz to 10 kHz. The sample was a mixture of aqueous solution of $CoFe_2O_4$ nanoparticle (10 μl) and 50% polyethylene glycol (PEG) (190 μl). This corresponds to about $2 \times 10^{12}$ nanoparticles and a magnetic volume fraction of 12 ppm. The dipolar interaction between magnetic nanoparticles was negligible due to the low volume fraction and the large interparticle distances.

As shown in FIG. 4, the magneto-optic data has a good correspondence to the data acquired by the PPMS. The peak frequency of the imaginary part of the ac susceptibility and the corresponding inflection frequency of the real part in both sets of data are the same. Furthermore, the two data sets overlap when the voltage signal from the lock-in amplifier is properly scaled. This scaling provides the calibration of the lock-in signal with respect to the absolute value of the ac susceptibility. In addition, the solid line is from the fit to the model of a convolution of Eq. (2) and a log-normal particle size distribution. This fit suggests the standard deviation σ of the size dispersion is 0.31. We note that the frequency scan for the magneto-optic method was acquired in ~10 min, while it took ~80 min for the PPMS.

To test the sensitivity of the setup, we measured the ac susceptibility of the samples with different concentration of magnetic nanoparticles, as shown in FIG. 5. The volume ratio between water and 50% PEG was adjusted to provide the same viscosity for different amounts of nanoparticle solutions. The peak positions of the imaginary part of the ac susceptibility for different nanoparticle concentrations are the same around 400 Hz. However, as the volume fraction of the nanoparticle decreases from 10 to 0.1 μl, the lock-in signal decreases accordingly and the noise level exceeds the peak signal at 0.1 μl. Considering the volume of the laser beam path in the 5-mm thick optical liquid cell, we estimate the minimum number of nanoparticles is $\sim 10^7$. When the same samples are used for the PPMS measurement (data not shown here), the ac susceptibility signal was not detectable with the nanoparticle concentration <0.1 μl, corresponding to $10^{10}$ nanoparticles and a volume fraction of ~0.1 ppm. Therefore, compared with the PPMS, our magneto-optic setup detects $10^3$ fewer nanoparticles. Furthermore, the minimum amount of sample with volume fraction of 0.1 ppm is only ~0.2 μl. FIG. 5 shows the peak voltage of the lock-in as a function of the nanoparticle concentration. The signal increases with the number of the nanoparticles in the low concentration regime, while it tends to decrease in the high concentration regime. The decrease at high concentration is due to the increased optical opaqueness, which attenuates the transmitted light signal. We also note that the agglomeration of the nanoparticles was not significant in our sample since the susceptibility signal before and after ultrasonic treatment showed little difference in contrast to the previous result.

FIG. 6 shows the peak frequency of the imaginary part of the ac susceptibility measured by the magneto-optic setup at different temperatures. An aqueous solution of $CoFe_2O_4$ nanoparticles (10 μl) was mixed with solvents with a composition of water (130 μl) and 50% PEG (70 μl). The peak frequency of $\chi''$ increases with increasing temperature. From Eqs. (1) and (2), it is clear that the peak frequency is proportional to temperature and inversely proportional to the viscosity. The temperature dependence of viscosity is given by:

$$\eta = A e^{E_V/kT} \quad (4)$$

where $E_V$ is the energy of viscosity. The fitting to the model shows a good correspondence to the experimental data. The value of $E_V$ from the fitting is $5.7 \times 10^{-20}$ J. This result implies that this technique can be used for sensing the local viscosity (or temperature). Note that the effect of the nanoparticles on the total viscosity is negligible since the volume fraction of nanoparticle is only ~10 ppm.

In conclusion, we have experimentally demonstrated a magneto-optic measurement of Brownian relaxation of magnetic nanoparticles suspended in liquid. We have applied the magneto-optic sensing technique to a micro-fluidic channel, such as the illustrated micro-fluidic cell 300, with rapid and sensitive detection with a small sample amount, and subsequent magnetic separation for detoxification. We have determined that this technique can be used for the detection of Brownian relaxation with time sweep as well as frequency sweep. We have also compared its sensitivity to that of a commercially available magneto-electric measurement system. A significant advantage of the magneto-optic method is that the technique is able to detect, for example, three orders of magnitude fewer particles within a confined region in a relatively short time. Further, in addition to the small sample requirement, the easy optical access to the micro-fluidic system enables potential lab-on-a-chip applications for viscosimetry and biosensing.

While the present invention has been described with reference to the details of the embodiments of the invention shown in the drawing, these details are not intended to limit the scope of the invention as claimed in the appended claims.

What is claimed is:

1. A biosensor comprising:
   a suspension of magnetic nanoparticles;
   an optical cell containing said suspension of magnetic nanoparticles;
   an electromagnet producing a weak magnetic field:
   a frequency oscillator modulating said weak magnetic field in a range between 10 Hz and 5 kHz, said modulated magnetic field being applied to said optical cell containing said suspension of magnetic nanoparticles;
   a light source applying a polarized incident light simultaneously with said modulated magnetic field to said suspension of magnetic nanoparticles; and
   a detector measuring modulated light intensity from said suspension of magnetic nanoparticles.

2. A biosensor as recited in claim 1 wherein said suspension of magnetic nanoparticles is contained within an optical liquid cell.

3. A biosensor as recited in claim 1 wherein said optical liquid cell is a micro-fluidic cell.

4. A biosensor as recited in claim 1 wherein said weak magnetic field is approximately 10 oersteds (Oe).

5. A biosensor as recited in claim 4 wherein said frequency oscillator is coupled to said electromagnet for applying said modulated magnetic field to said optical cell containing said suspension of magnetic nanoparticles.

6. A biosensor as recited in claim 1 wherein said light source includes a laser.

7. A biosensor as recited in claim 6 wherein said laser includes a Krypton laser.

8. A biosensor as recited in claim 6 further includes a polarizer in a laser beam path.

9. A biosensor as recited in claim 6 further includes a lens in a laser beam path for focusing the incident light: said laser beam being focused to approximately 200 micrometers.

10. A biosensor as recited in claim 6 further includes a plate adjusting a polarization angle of the incident light.

11. A biosensor as recited in claim 10 wherein said plate includes a quarter-wave plate adjusting a polarization angle of the incident light to a Faraday angle within a weak field linear regime.

12. A biosensor as recited in claim 1 wherein said detector includes a photo detector, said photo detector amplifying modulated intensity due to a magneto-optic response.

13. A biosensor as recited in claim 1 wherein said detector further includes a lock-in amplifier measuring in-phase and out-of-phase components of the modulation light intensity.

14. A biosensor as recited in claim 13 wherein said lock-in amplifier measures the in-phase and out-of-phase components of the modulation light intensity, proportional to a Faraday rotation of the modulation light intensity.

15. A biosensor as recited in claim 1 wherein said optical cell includes a micro-fluidic cell, said micro-fluidic cell including a micro-fluidic capillary network.

16. A biosensor as recited in claim 15 wherein said micro-fluidic capillary network includes a capillary receiving a solution of magnetic nanoparticles, and a capillary receiving a target molecule solution.

17. A biosensor as recited in claim 16 wherein said micro-fluidic capillary network includes a µ-stripline.

18. A biosensor as recited in claim 16 wherein said micro-fluidic capillary network receives an applied laser beam.

* * * * *